United States Patent [19]
Ekdahl

[11] Patent Number: 5,674,211
[45] Date of Patent: Oct. 7, 1997

[54] METHOD FOR MANUFACTURING A MATERIAL SUITABLE FOR USE AS A TOP SHEET OF AN ABSORBENT DISPOSABLE ARTICLE, AND ONE SUCH MATERIAL

[75] Inventor: Joakim Ekdahl, Mölndal, Sweden

[73] Assignee: Mölnlycke AB, Gothenborg, Sweden

[21] Appl. No.: 335,881

[22] PCT Filed: May 18, 1993

[86] PCT No.: PCT/SE93/00442
§ 371 Date: Nov. 18, 1994
§ 102(e) Date: Nov. 18, 1994

[87] PCT Pub. No.: WO93/22995
PCT Pub. Date: Nov. 25, 1993

[30] Foreign Application Priority Data
May 21, 1992 [SE] Sweden .................... 9201604

[51] Int. Cl.$^6$ ............... A61F 13/15; B32B 3/10; B29C 43/22
[52] U.S. Cl. ............ 604/383; 604/358; 604/378; 264/504; 264/DIG. 70; 428/131; 428/138
[58] Field of Search ............ 264/504, DIG. 70; 604/383, 358, 378; 428/131, 134, 137, 138, 304.4

[56] References Cited

U.S. PATENT DOCUMENTS

| | | |
|---|---|---|
| 4,041,949 | 8/1977 | Kozak . |
| 4,495,133 | 1/1985 | Sugihara et al. . |
| 4,704,112 | 11/1987 | Suzuki et al. . |
| 4,726,976 | 2/1988 | Karami et al. . |
| 4,781,962 | 11/1988 | Zamarripa et al. . |
| 4,995,930 | 2/1991 | Merz et al. . |

FOREIGN PATENT DOCUMENTS

| | | |
|---|---|---|
| 0 057 484 | 11/1982 | European Pat. Off. . |
| 970932 | 9/1964 | United Kingdom . |
| 1063066 | 3/1967 | United Kingdom . |
| 1100485 | 1/1968 | United Kingdom . |

*Primary Examiner*—Mary Beth Jones
*Assistant Examiner*—Dennis Ruhl
*Attorney, Agent, or Firm*—Burns, Doane, Swecker & Mathis, L.L.P.

[57] ABSTRACT

In a method of manufacturing material suitable for use as a top sheet in an absorbent disposable article, such as a sanitary napkin, an incontinence guard or a diaper, a laminate (1) comprised of a plastic film (2) and a layer of non-woven material (3) on at least one side of the plastic film is applied to a perforated supportive device (6) with one layer of non-woven material facing towards the supportive device. The plastic film is heated to a temperature above its softening temperature and there is generated between the two mutually opposing sides of the laminate a pressure difference of such magnitude that the plastic film will rupture within the regions of the holes in the supportive device so as to form openings (10) which lead to the associated non-woven material. A soft and smooth, liquid-permeable top sheet material is achieved.

23 Claims, 1 Drawing Sheet

METHOD FOR MANUFACTURING A MATERIAL SUITABLE FOR USE AS A TOP SHEET OF AN ABSORBENT DISPOSABLE ARTICLE, AND ONE SUCH MATERIAL

BACKGROUND OF THE INVENTION

1. Field of the Invention

The present invention relates to a method for manufacturing a material which is suitable for use as the top sheet of an absorbent disposable article, such as a sanitary napkin, an incontinence guard or a diaper, and also to material manufactured in accordance with the method.

2. Description of Related Art

Absorbent disposable articles are often provided with a top sheet on the side of the article which lies proximal to the wearer in use. Consequently, the top sheet should be felt to be soft and dry by the wearer. In order to provide a feeling of dryness to the wearer, perforated hydrophobic plastic films are sometimes used closest to the wearer's body. It is also known to provide in the film holes of a conical or straight tubular configuration, so as to obtain capillaries which reduce the risk of re-wetting, i.e. to reduce the tendency of fluid that has been absorbed in an underlying absorbent body flowing back through the perforations in the plastic film when the absorbent body is subjected to external pressure forces. Another known method of alleviating risk of re-wetting involves providing a spacing sheet between the plastic sheet and the absorbent body and by forming the top sheet from several different layers of material.

One example of a composite top sheet is comprised of a perforated plastic film which has been laminated to a layer of non-woven material by hot-calendaring, ultrasonic welding or gluing. Such top sheets have good draining ability and relatively low re-wetting tendencies, but are relatively stiff and often even rough.

OBJECTS AND SUMMARY

An object of the present invention is to provide top sheet material which in addition to possessing good drainage, re-wetting and liquid dispersion properties is also soft and smooth.

This object is achieved in accordance with the invention with a method of the kind defined in the introduction which is characterized in that a laminate comprising a plastic film and a layer of non-woven material on at least one side of the plastic film is applied to a perforated supportive device with the non-woven layer or one of the non-woven layers of the laminate facing towards said device; in that the plastic film is heated to a temperature above its softening temperature; and in that there is generated between the two mutually opposing sides of the laminate a pressure difference of such magnitude as to cause the plastic film to rupture in the regions of the perforations in the supportive device, so as to form openings which lead to the associated non-woven layer or layers. By forming the perforations in the plastic film subsequent to having laminated the film with the non-woven layer or layers, it is possible to chose other laminating methods, such as extrusion coating of the non-woven material with plastic film, than the method of laminating a pre-perforated plastic film with a layer of non-woven material, therewith enabling a softer top sheet material to be produced. In addition to simplifying the laminating method, the invention also simplifies the perforating method, since the pieces of film which break away from the plastic film seat firmly in the non-woven material, thereby obviating the need to handle waste or to clean the perforated supportive device when practicing the inventive method.

The invention also relates to top sheet material manufactured in accordance with the method, this material being characterized in that the non-woven material on one side of the plastic film includes depressions or hollows which are located beneath the holes in the plastic film and the bottom surfaces of which are covered with material that has broken away from the plastic film. Because the bottom surfaces of the depressions or hollows are covered at least over larger parts thereof with a fluid-impervious material, liquid or fluid discharged by the wearer will spread laterally in the non-woven material. The top sheet also becomes more attractive from an aesthetic point of view, since the film material present in the depressions will cover those parts of the non-woven material which would otherwise be visible when viewing the top sheet.

According to one advantageous embodiment of the invention, the laminate is comprised of a non-woven material onto which a covering of plastic material has been extruded. According to another advantageous embodiment of the invention, the laminate is a three-layer structure comprised of a plastic film which is extrusion-laminated between two layers of non-woven material.

BRIEF DESCRIPTION OF THE DRAWINGS

The invention will now be described in more detail with reference to an exemplifying embodiment thereof and also with reference to the accompanying drawings, in which.

DETAILED DESCRIPTION OF PREFERRED EMBODIMENTS

Figure 1:
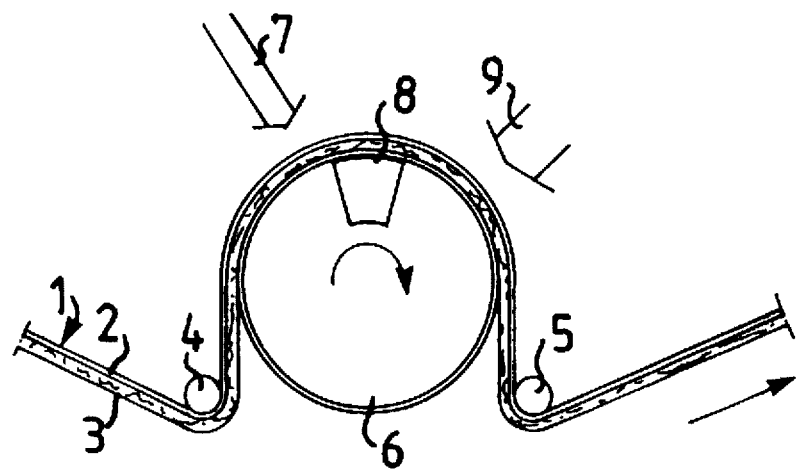
FIG. 1 illustrates schematically apparatus suitable for manufacturing top sheet material in accordance with the invention.

FIG. 1 illustrates an exemplifying embodiment of the inventive method, in which a laminate 1 comprised of an impervious plastic film 2 and a layer of non-woven material 3 is passed over part of the periphery of a rotating screen or perforated drum 6, wherewith the laminate is held against the drum with the aid of guide rollers 4, 5. As will be seen from the figure, the non-woven side of the laminate 1 faces towards the drum and the plastic film 2 lies furthest therefrom. The perforated drum may be of any known kind used for perforating film material for use as top sheet material. The drum houses a stationary suction box 8 and a plastic-film heating device 7 is mounted immediately upstream of the suction box, as seen in the direction of movement of the laminate, this direction being indicated with an arrow placed beneath the part of the laminate leaving from the drum in FIG. 1. This heating device may create in hot air exiting from a hot air delivery blade or a broad slot nozzle which functions to heat the plastic film 2 uniformly over the whole of its width.

As the laminate 1 passes the heating source 7, the plastic film is heated to a temperature such that as it passes the suction box 8 the temperature of the plastic film will be higher than its softening temperature. As the laminate 1 reaches the suction box 8, in which a high subpressure prevails, the laminate is sucked into the drum perforations.

Figure 2:
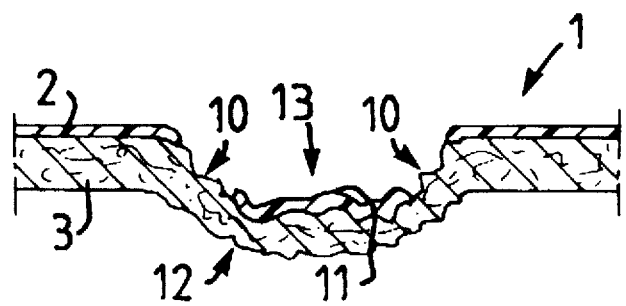
FIG. 2 is a schematic cross-sectional view showing a small part of an inventive first top-sheet material, on a greatly exaggerated scale.

This causes the plastic film to rupture, so as to form openings 10 which lead to the underlying non-woven material 3, see FIG. 2.

The laminate is cooled in some suitable manner after having passed the suction box 8, for instance with the aid of cold air, symbolized with the arrow 9 in FIG. 1.

FIG. 2 illustrates an exemplifying embodiment of top sheet material manufactured in accordance with the aforedescribed method. As will be seen from the figure, the non-woven material 3 contains depressions or hollows 12 (only one of which is shown in FIG. 2) in each part of the material that was located above a perforation in the drum 6 during the process of manufacture, and openings 10 in the plastic film are located at the edges of respective depressions and enable fluid to flow to the non-woven material 3. A residual piece of plastic film 11 is located at the bottom of each depression. The plastic film thus presents holes 13 in its surface plane.

One possible explanation as to why the plastic film ruptures at said edge regions may be that the non-woven material is compressed very rapidly against the edges of the perforations in the drum when applying said large pressure difference, and that the plastic film laminated to the fibre material is unable to follow the rapid deformation movement of the non-woven material in this edge region and therewith ruptures at said region. Subsequent to the plastic film having ruptured, air is able to flow through the resultant opening or openings and the total pressure force acting on the layer of non-woven material decreases with the pressure drop across those parts of the non-woven material through which air flows. The ruptured piece 11 of film material is free to shrink together after having broken loose from the remainder of the plastic film.

It will be evident from the aforegoing that the mechanical strength of the non-woven material must be greater than the mechanical strength of the plastic film subsequent to the laminate 1 having passed the heat source 7 and reached the suction box 8. This is conveniently achieved by choosing a non-woven material which contains a large proportion of fibres whose softening temperature is considerably higher than the softening temperature of the plastic film used. The impervious plastic film used in the laminate may, for instance, be a polyolefin, such as polyethylene, while the non-woven material may contain a mixture of 50% polypropylene and 50% bicomponent fibres comprised of a polypropylene core encased in a polyethylene casing. According to the present invention, the laminate is heated by blowing hot air at a temperature of 300°–500° C. onto the plastic-film side of the laminate, which means that the non-woven material will not be heated to any appreciable extent.

The laminate 1 is conveniently comprised of an extrusion-coated non-woven material, i.e. is laminated by extruding continuously a molten film onto a moving non-woven web. Such a laminate will be very soft and is well suited as a starting material in the manufacture of top sheet material. Naturally, it is conceivable within the scope of the invention to integrate the actual laminating of the plastic film and non-woven material and thereby eliminate the need of the heating source 7 of the FIG. 1 example. In this case, means other than the rollers 4, 5 of the FIG. 1 embodiment must be used to hold the non-woven material in contact with the screen. It will be understood that other modifications to the apparatus for producing holes in the laminate are possible without departing from the inventive concept.

For instance, the perforated drum may be replaced with some other suitable perforated supportive device.

Furthermore, it is possible to generate the pressure difference with means other than a suction box, for instance holes can be blown into the film instead of being sucked thereinto.

Figure 3:
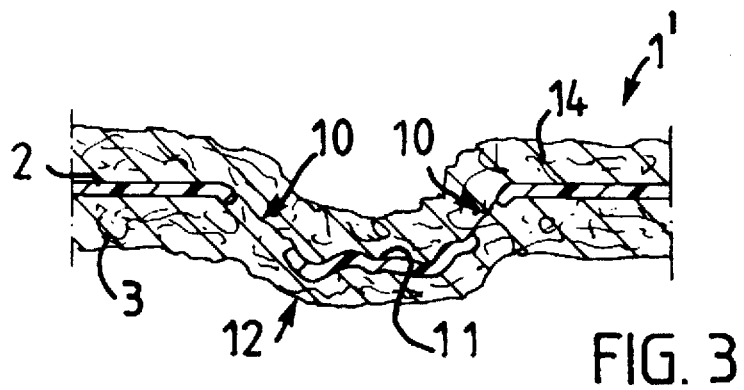
FIG. 3 is a view similar to FIG. 2 of an inventive second top-sheet material.

In order to provide a top sheet which will have the feeling of textile material against the skin of the wearer, the laminate may comprise a further layer of non-woven material. A second layer of non-woven material may be be laminated on the side of the plastic film opposite to that on which the aforesaid layer of non-woven material is laminated. FIG. 3 illustrates a laminate 1', which consists in a first layer 3 of non-woven material, a plastic film 2, and a second layer 14 of non-woven material, in that order. Thus, when the laminate 1' is used as a top sheet in a disposable article, the second layer 14 will constitute the layer that lies in contact with the wearer's skin, which is an advantage since non-woven material is similar to textile material and is therefore skin-friendly.

A three-layer laminate 1' of the aforedescribed construction can be produced, for instance, by an extrusion-laminating process in which a plastic film, for instance a polyethylene film, is extruded between two material layers, for instance between two layers of non-woven material. The plastic film thereby acts as a binding layer between the two non-woven layers. These two layers may consist of non-woven material of mutually the same or mutually different properties. The correct choice of non-woven material and plastic film will enable the inventive method to be used to form openings in a plastic film of such an extrusion laminate. The earlier described inventive method can be applied advantageously in-line with the actual extrusion laminating process, in the same way as that previously described with reference to the FIG. 2 embodiment with regard to a laminate comprising only one non-woven layer. The softening temperature of the fibres in the second non-woven material 14 will preferably be higher than the temperature to which the laminate is heated in the heating process, so that openings will only occur in the plastic film and not in the non-woven material. This is particularly important, as the second non-woven layer 14 will face towards the heating source and cannot be shaded by the plastic film, as is the first non-woven layer 3 in beth the extrusion coated laminate of the FIG. 2 embodiment and the extrusion laminate shown in FIG. 3.

I claim:

1. A method for manufacturing a top sheet of an absorbent disposable article, such as a sanitary napkin, an incontinence guard or a diaper, comprising the steps of:

applying a laminate comprised of a plastic film and a layer of non-woven material on at least one side of the plastic film to a perforated supportive device with the non-woven layer facing towards the supportive device;

heating the plastic film to a temperature above its softening temperature; and generating a pressure difference of such magnitude between two sides of the laminate as to cause the plastic film to rupture within regions corresponding to perforations in said supportive device, so as to form openings which lead to the layer of non-woven material.

2. A method according to claim 1, further comprising the step of applying a molten plastic film to a moving non-woven material and thereafter subjecting the non-woven material and the plastic film to subpressure in a stationary suction box mounted beneath the perforated supportive device.

3. A method according to claim 2, further comprising the step of heating the plastic film applied to the moving non-woven material immediately prior to the laminate reaching the suction box.

4. A method according to claim 1, further comprising the step of cooling the laminate subsequent to having applied said pressure thereto.

5. A method according to claim 1, further comprising the step of heating the plastic film immediately prior to reaching the suction box by blowing hot air onto the plastic film.

6. A top sheet material for an absorbent disposable article, such as a sanitary napkin, an incontinence guard or a diaper, said material comprising:

a laminate which includes an impervious plastic film and a layer of non-woven material on at least one side of the plastic film, said plastic film having been made fluid-permeable by providing said film with a plurality of holes, the layer of non-woven material on one side of the plastic film containing depressions or hollows which are located beneath the holes in the plastic film and the depressions or hollows having bottoms which are lined with material that has broken away from said plastic film.

7. The material according to claim 6, wherein the laminate is comprised of an extrusion coated layer of non-woven material.

8. A top sheet material for an absorbent disposable article, such as a sanitary napkin, an incontinence guard or a diaper, said material comprising:

a laminate which includes an impervious plastic film and a layer of non-woven material on at least one side of the plastic film, wherein the laminate is comprised of an extrusion laminate which includes a plastic film extruded between two layers of non-woven material, said plastic film having been made fluid-permeable by providing said film with a plurality of holes, the layer of non-woven material on one side of the plastic film containing depressions or hollows which are located beneath the holes in the plastic film and the depressions or hollows having bottoms which are lined with material that has broken away from said plastic film.

9. The material according to claim 7, wherein the non-woven layer contains a large proportion of fibres whose softening temperature is higher than the softening temperature of the plastic film.

10. The material according to claim 9, wherein the plastic film is comprised of polyethylene and the layer of non-woven material is comprised of a mixture of poly-propylene fibres and bicomponent fibres which are comprised of polypropylene cores encased in a polyethylene casing.

11. A method according to claim 2, further comprising the step of cooling the laminate subsequent to having applied said pressure thereto.

12. A method according to claim 3, further comprising the step of cooling the laminate subsequent to having applied said pressure thereto.

13. A method according to claim 2, further comprising the step of heating the plastic film immediately prior to reaching the suction box by blowing hot air onto the plastic film.

14. A method according to claim 3, further comprising the step of heating the plastic film immediately prior to reaching the suction box by blowing hot air onto the plastic film.

15. A method according to claim 4, further comprising the step of heating the plastic film immediately prior to reaching the suction box by blowing hot air onto the plastic film.

16. The material according to claim 8, wherein the non-woven layers contain a large proportion of fibres whose softening temperature is higher than the softening temperature of the plastic film.

17. The material according to claim 16, wherein the plastic film is comprised of polyethylene and the layers of non-woven material are comprised of a mixture of polypropylene fibres and bicomponent fibres which are comprised of a polypropylene core encased in a polyethylene casing.

18. The method according to claim 1, wherein the pressure difference forms depressions or hollows in the layer of non-woven material within the regions corresponding to perforations in said supportive device.

19. The method according to claim 1, wherein the non-woven material is comprised of a mixture of poly-propylene fibers and bicomponent fibers which are comprised of polypropylene cores encased in a polyethylene casing.

20. A method for manufacturing a top sheet of an absorbent disposable article comprising:

applying a laminate comprised of a plastic film and a layer of non-woven material on at least one side of the plastic film to a perforated supportive device with the non-woven layer facing towards the supportive device;

heating the plastic film to a temperature above its softening temperature; and generating a pressure difference of such magnitude between opposite sides of the laminate as to cause the plastic film to rupture above the perforations in said supportive device so as to form openings and to cause depressions or hollows to form in the non-woven layer beneath the openings, the openings leading into the non-woven layer.

21. The method according to claim 20, wherein the non-woven material is comprised of a mixture of poly-propylene fibers and bicomponent fibers which are comprised of poly-propylene cores encased in a polyethylene casing.

22. The material according to claim 6, wherein the holes in the plastic film are formed by mechanical failure.

23. The material according to claim 6, wherein the material which lines the bottoms of the depressions or hollows is a non-melted portion of the plastic film which has broken away from a remainder of the plastic film.

* * * * *